(12) United States Patent
Kendall

(10) Patent No.: US 11,373,752 B2
(45) Date of Patent: Jun. 28, 2022

(54) DETECTION OF MISUSE OF A BENEFIT SYSTEM

(71) Applicant: Palantir Technologies Inc., Palo Alto, CA (US)

(72) Inventor: Logan Kendall, Seattle, WA (US)

(73) Assignee: Palantir Technologies Inc., Palo Alto, CA (US)

( * ) Notice: Subject to any disclaimer, the term of this patent is extended or adjusted under 35 U.S.C. 154(b) by 562 days.

(21) Appl. No.: 15/824,852

(22) Filed: Nov. 28, 2017

(65) Prior Publication Data

US 2018/0181717 A1 Jun. 28, 2018

Related U.S. Application Data

(60) Provisional application No. 62/438,185, filed on Dec. 22, 2016.

(51) Int. Cl.
*G16H 40/20* (2018.01)
*G16H 10/60* (2018.01)
(Continued)

(52) U.S. Cl.
CPC ............ *G16H 40/20* (2018.01); *G06Q 10/00* (2013.01); *G06Q 10/10* (2013.01); *G06Q 10/105* (2013.01);
(Continued)

(58) Field of Classification Search
CPC .. G06F 19/328; G06F 19/325; G06F 19/3475; G16H 40/20; G16H 10/60;
(Continued)

(56) References Cited

U.S. PATENT DOCUMENTS

| 5,515,488 A | 5/1996 | Hoppe et al. |
| 5,893,072 A | 4/1999 | Zizzamia |

(Continued)

FOREIGN PATENT DOCUMENTS

| CN | 102546446 | 7/2012 |
| CN | 103167093 | 6/2013 |

(Continued)

OTHER PUBLICATIONS

"HunchLab: Heat Map and Kernel Density Calculation for Crime Analysis," Azavea Journal, printed from www.azavea.com/blogs/newsletter/v4i4/kernel-density-capabilities-added-to-hunchlab/ on Sep. 9, 2014, 2 pages.

(Continued)

*Primary Examiner* — Rachel L. Porter
*Assistant Examiner* — Steven G Sanghera
(74) *Attorney, Agent, or Firm* — Sheppard Mullin Richter & Hampton LLP

(57) ABSTRACT

Systems and methods are provided for automatically detecting misuse of a benefit system. Information relating to benefit provision (e.g., receiver information, service performed, equipment used, materials provided, provider information, etc.) may be parsed from claims data to determine patterns for benefit receivers and/or benefit providers. The patterns may be analyzed to determine specific patterns indicative of fraud/benefit abuse and the particular benefit receivers/providers/events may be tagged as a lead for investigation.

20 Claims, 6 Drawing Sheets

(51) Int. Cl.
*G06Q 10/10* (2012.01)
*G16H 70/20* (2018.01)
*G06Q 10/00* (2012.01)
*G06Q 40/08* (2012.01)

(52) U.S. Cl.
CPC ............. *G06Q 40/08* (2013.01); *G16H 10/60* (2018.01); *G16H 70/20* (2018.01)

(58) Field of Classification Search
CPC ........ G16H 70/20; G06Q 10/00; G06Q 10/10; G06Q 10/105
See application file for complete search history.

(56) References Cited

U.S. PATENT DOCUMENTS

| | | | |
|---|---|---|---|
| 6,232,971 B1 | 5/2001 | Haynes | |
| 6,430,305 B1 | 8/2002 | Decker | |
| 6,505,196 B2 | 1/2003 | Drucker et al. | |
| 6,523,019 B1 | 2/2003 | Borthwick | |
| 6,820,135 B1 | 11/2004 | Dingman | |
| 6,826,536 B1* | 11/2004 | Forman | G06F 19/328 705/3 |
| 6,978,419 B1 | 12/2005 | Kantrowitz | |
| 6,980,984 B1 | 12/2005 | Huffman et al. | |
| 7,168,039 B2 | 1/2007 | Bertram | |
| 7,383,239 B2 | 6/2008 | Bonissone | |
| 7,418,431 B1 | 8/2008 | Nies et al. | |
| 7,461,077 B1 | 12/2008 | Greenwood | |
| 7,493,264 B1* | 2/2009 | Kelly | G06Q 10/06 705/2 |
| 7,617,232 B2 | 11/2009 | Gabbert et al. | |
| 7,756,843 B1 | 7/2010 | Palmer | |
| 7,765,489 B1 | 7/2010 | Shah | |
| 7,813,937 B1 | 10/2010 | Pathria et al. | |
| 7,827,045 B2 | 11/2010 | Madill et al. | |
| 7,899,796 B1 | 3/2011 | Borthwick et al. | |
| 7,917,376 B2 | 3/2011 | Bellin et al. | |
| 7,941,321 B2 | 5/2011 | Greenstein et al. | |
| 7,966,199 B1 | 6/2011 | Frasher | |
| 8,036,971 B2 | 10/2011 | Aymeloglu et al. | |
| 8,037,046 B2 | 10/2011 | Udezue et al. | |
| 8,046,283 B2 | 10/2011 | Burns | |
| 8,054,756 B2 | 11/2011 | Chand et al. | |
| 8,214,232 B2 | 7/2012 | Tyler et al. | |
| 8,214,490 B1 | 7/2012 | Vos et al. | |
| 8,229,902 B2 | 7/2012 | Vishniac et al. | |
| 8,290,838 B1 | 10/2012 | Thakur et al. | |
| 8,301,464 B1 | 10/2012 | Cave et al. | |
| 8,302,855 B2 | 11/2012 | Ma et al. | |
| 8,386,377 B1 | 2/2013 | Xiong et al. | |
| 8,473,454 B2 | 6/2013 | Evanitsky et al. | |
| 8,484,115 B2 | 7/2013 | Aymeloglu et al. | |
| 8,489,623 B2 | 7/2013 | Jain et al. | |
| 8,489,641 B1 | 7/2013 | Seefeld et al. | |
| 8,515,912 B2 | 8/2013 | Garrod et al. | |
| 8,527,461 B2 | 9/2013 | Ducott, III et al. | |
| 8,577,911 B1 | 11/2013 | Stepinski et al. | |
| 8,578,500 B2 | 11/2013 | Long | |
| 8,589,273 B2 | 11/2013 | Creeden et al. | |
| 8,639,522 B2 | 1/2014 | Pathria et al. | |
| 8,655,687 B2 | 2/2014 | Zizzamia | |
| 8,682,696 B1 | 3/2014 | Shanmugam | |
| 8,688,573 B1 | 4/2014 | Ruknoic et al. | |
| 8,744,890 B1 | 6/2014 | Bernier | |
| 8,799,313 B2 | 8/2014 | Satlow | |
| 8,799,799 B1 | 8/2014 | Cervelli et al. | |
| 8,806,355 B2 | 8/2014 | Twiss et al. | |
| 8,812,960 B1 | 8/2014 | Sun et al. | |
| 8,924,388 B2 | 12/2014 | Elliot et al. | |
| 8,924,389 B2 | 12/2014 | Elliot et al. | |
| 8,938,686 B1 | 1/2015 | Erenrich et al. | |
| 8,949,164 B1 | 2/2015 | Mohler | |
| 9,031,317 B2* | 5/2015 | Yakubovich | G06T 15/20 382/159 |
| 9,069,842 B2 | 6/2015 | Melby | |
| 9,100,428 B1 | 8/2015 | Visbal | |
| 9,111,281 B2 | 8/2015 | Stibel et al. | |
| 9,129,219 B1 | 9/2015 | Robertson et al. | |
| 9,256,664 B2 | 2/2016 | Chakerian et al. | |
| 9,280,618 B1 | 3/2016 | Bruce et al. | |
| 9,286,373 B2 | 3/2016 | Elliot et al. | |
| 9,335,911 B1 | 5/2016 | Elliot et al. | |
| 2002/0065708 A1 | 5/2002 | Senay et al. | |
| 2002/0095360 A1 | 7/2002 | Joao | |
| 2002/0095658 A1 | 7/2002 | Shulman | |
| 2002/0103705 A1 | 8/2002 | Brady | |
| 2002/0147805 A1 | 10/2002 | Leshem et al. | |
| 2003/0036927 A1 | 2/2003 | Bowen | |
| 2003/0126102 A1 | 7/2003 | Borthwick | |
| 2003/0163352 A1 | 8/2003 | Surpin et al. | |
| 2004/0034570 A1 | 2/2004 | Davis | |
| 2004/0059736 A1* | 3/2004 | Willse | G06F 40/20 |
| 2004/0111480 A1 | 6/2004 | Yue | |
| 2004/0126840 A1 | 7/2004 | Cheng et al. | |
| 2004/0153418 A1 | 8/2004 | Hanweck | |
| 2004/0236688 A1 | 11/2004 | Bozeman | |
| 2005/0010472 A1 | 1/2005 | Quatse et al. | |
| 2005/0028094 A1 | 2/2005 | Allyn | |
| 2005/0086207 A1 | 4/2005 | Heuer et al. | |
| 2005/0108063 A1 | 5/2005 | Madill et al. | |
| 2005/0125715 A1 | 6/2005 | Di Franco et al. | |
| 2005/0149527 A1 | 7/2005 | Berlin | |
| 2005/0154628 A1 | 7/2005 | Eckart et al. | |
| 2005/0154769 A1 | 7/2005 | Eckart et al. | |
| 2005/0182654 A1 | 8/2005 | Abolfathi et al. | |
| 2006/0026120 A1 | 2/2006 | Carolan et al. | |
| 2006/0026170 A1 | 2/2006 | Kreitler et al. | |
| 2006/0080139 A1 | 4/2006 | Mainzer | |
| 2006/0080283 A1 | 4/2006 | Shipman | |
| 2006/0129746 A1 | 6/2006 | Porter | |
| 2006/0142949 A1 | 6/2006 | Helt | |
| 2006/0143034 A1 | 6/2006 | Rothermel | |
| 2006/0143075 A1 | 6/2006 | Carr et al. | |
| 2006/0143079 A1 | 6/2006 | Basak et al. | |
| 2006/0149596 A1 | 7/2006 | Surpin et al. | |
| 2006/0178915 A1 | 8/2006 | Chao | |
| 2006/0241974 A1 | 10/2006 | Chao et al. | |
| 2007/0000999 A1 | 1/2007 | Kubo et al. | |
| 2007/0011304 A1 | 1/2007 | Error | |
| 2007/0038646 A1 | 2/2007 | Thota | |
| 2007/0136095 A1 | 6/2007 | Weinstein | |
| 2007/0150801 A1 | 6/2007 | Chidlovskii et al. | |
| 2007/0156673 A1 | 7/2007 | Maga | |
| 2007/0162454 A1 | 7/2007 | D'Albora et al. | |
| 2007/0185867 A1 | 8/2007 | Maga | |
| 2007/0192122 A1 | 8/2007 | Routson et al. | |
| 2007/0192143 A1 | 8/2007 | Krishnan et al. | |
| 2007/0284433 A1 | 12/2007 | Domenica et al. | |
| 2007/0299697 A1 | 12/2007 | Friedlander et al. | |
| 2008/0065655 A1 | 3/2008 | Chakravarthy et al. | |
| 2008/0069081 A1 | 3/2008 | Chand et al. | |
| 2008/0077642 A1 | 3/2008 | Carbone et al. | |
| 2008/0103996 A1 | 5/2008 | Forman et al. | |
| 2008/0155440 A1 | 6/2008 | Trevor et al. | |
| 2008/0172257 A1 | 7/2008 | Bisker et al. | |
| 2008/0195417 A1 | 8/2008 | Surpin et al. | |
| 2008/0195421 A1 | 8/2008 | Ludwig et al. | |
| 2008/0208735 A1 | 8/2008 | Balet et al. | |
| 2008/0222295 A1 | 9/2008 | Robinson et al. | |
| 2008/0235199 A1 | 9/2008 | Li et al. | |
| 2008/0243711 A1 | 10/2008 | Aymeloglu et al. | |
| 2008/0249820 A1 | 10/2008 | Pathria | |
| 2008/0255973 A1 | 10/2008 | El Wade et al. | |
| 2008/0270328 A1 | 10/2008 | Lafferty et al. | |
| 2008/0281819 A1 | 11/2008 | Tenenbaum et al. | |
| 2008/0294663 A1 | 11/2008 | Heinley et al. | |
| 2008/0313132 A1 | 12/2008 | Hao et al. | |
| 2009/0043801 A1 | 2/2009 | LeClair | |
| 2009/0070162 A1 | 3/2009 | Leonelli et al. | |
| 2009/0076845 A1 | 3/2009 | Bellin et al. | |
| 2009/0094166 A1 | 4/2009 | Aymeloglu et al. | |
| 2009/0094270 A1 | 4/2009 | Alirez et al. | |
| 2009/0106178 A1 | 4/2009 | Chu | |

(56) References Cited

U.S. PATENT DOCUMENTS

| | | |
|---|---|---|
| 2009/0112745 A1 | 4/2009 | Stefanescu |
| 2009/0125359 A1 | 5/2009 | Knapic |
| 2009/0125459 A1 | 5/2009 | Norton et al. |
| 2009/0132953 A1 | 5/2009 | Reed et al. |
| 2009/0157732 A1 | 6/2009 | Hao et al. |
| 2009/0187546 A1 | 7/2009 | Whyte et al. |
| 2009/0187548 A1 | 7/2009 | Ji et al. |
| 2009/0216562 A1 | 8/2009 | Faulkner et al. |
| 2009/0240529 A1 | 9/2009 | Chess et al. |
| 2009/0249244 A1 | 10/2009 | Robinson et al. |
| 2009/0254842 A1 | 10/2009 | Leacock et al. |
| 2009/0259636 A1 | 10/2009 | Labrou et al. |
| 2009/0271343 A1 | 10/2009 | Vaiciulis et al. |
| 2009/0281839 A1 | 11/2009 | Lynn et al. |
| 2009/0307049 A1 | 12/2009 | Elliott et al. |
| 2009/0313463 A1 | 12/2009 | Pang et al. |
| 2009/0319418 A1 | 12/2009 | Herz |
| 2009/0319515 A1 | 12/2009 | Minton et al. |
| 2009/0319891 A1 | 12/2009 | MacKinlay |
| 2010/0030722 A1 | 2/2010 | Goodson et al. |
| 2010/0031141 A1 | 2/2010 | Summers et al. |
| 2010/0042922 A1 | 2/2010 | Bradateanu et al. |
| 2010/0057622 A1 | 3/2010 | Faith et al. |
| 2010/0070842 A1 | 3/2010 | Aymeloglu et al. |
| 2010/0098318 A1 | 4/2010 | Anderson |
| 2010/0106752 A1 | 4/2010 | Eckardt et al. |
| 2010/0114887 A1 | 5/2010 | Conway et al. |
| 2010/0131502 A1 | 5/2010 | Fordham |
| 2010/0161735 A1 | 6/2010 | Sharma |
| 2010/0191563 A1 | 7/2010 | Schlaifer et al. |
| 2010/0211535 A1 | 8/2010 | Rosenberger |
| 2010/0235915 A1 | 9/2010 | Memon et al. |
| 2010/0262688 A1 | 10/2010 | Hussain et al. |
| 2010/0280851 A1 | 11/2010 | Merkin |
| 2010/0293174 A1 | 11/2010 | Bennett et al. |
| 2010/0312837 A1 | 12/2010 | Bodapati et al. |
| 2010/0324929 A1 | 12/2010 | Petrasich et al. |
| 2011/0040776 A1 | 2/2011 | Najm et al. |
| 2011/0061013 A1 | 3/2011 | Bilicki et al. |
| 2011/0078173 A1 | 3/2011 | Seligmann et al. |
| 2011/0093327 A1 | 4/2011 | Fordyce, III et al. |
| 2011/0099133 A1 | 4/2011 | Chang et al. |
| 2011/0153384 A1 | 6/2011 | Horne et al. |
| 2011/0161409 A1 | 6/2011 | Nair |
| 2011/0173093 A1 | 7/2011 | Psota et al. |
| 2011/0179048 A1 | 7/2011 | Satlow |
| 2011/0208565 A1 | 8/2011 | Ross et al. |
| 2011/0208724 A1 | 8/2011 | Jones et al. |
| 2011/0213655 A1 | 9/2011 | Henkin |
| 2011/0218955 A1 | 9/2011 | Tang |
| 2011/0246229 A1 | 10/2011 | Pacha |
| 2011/0270604 A1 | 11/2011 | Qi et al. |
| 2011/0270834 A1 | 11/2011 | Sokolan et al. |
| 2011/0289397 A1 | 11/2011 | Eastmond et al. |
| 2011/0295649 A1 | 12/2011 | Fine |
| 2011/0314007 A1 | 12/2011 | Dassa et al. |
| 2011/0314024 A1 | 12/2011 | Chang et al. |
| 2012/0004894 A1 | 1/2012 | Butler |
| 2012/0004904 A1 | 1/2012 | Shin et al. |
| 2012/0011238 A1 | 1/2012 | Rathod |
| 2012/0011245 A1 | 1/2012 | Gillette et al. |
| 2012/0022945 A1 | 1/2012 | Falkenborg et al. |
| 2012/0054284 A1 | 3/2012 | Rakshit |
| 2012/0059853 A1 | 3/2012 | Jagota |
| 2012/0065987 A1 | 3/2012 | Farooq et al. |
| 2012/0066166 A1 | 3/2012 | Curbera et al. |
| 2012/0079363 A1 | 3/2012 | Folting et al. |
| 2012/0084117 A1 | 4/2012 | Tavares et al. |
| 2012/0084184 A1 | 4/2012 | Raleigh |
| 2012/0084287 A1 | 4/2012 | Lakshminarayan et al. |
| 2012/0089606 A1 | 4/2012 | Eshwar et al. |
| 2012/0131512 A1 | 5/2012 | Takeuchi et al. |
| 2012/0144335 A1 | 6/2012 | Abeln et al. |
| 2012/0158527 A1 | 6/2012 | Cannelongo et al. |
| 2012/0159362 A1 | 6/2012 | Brown et al. |
| 2012/0173381 A1 | 7/2012 | Smith |
| 2012/0197657 A1 | 8/2012 | Prodanovic |
| 2012/0197660 A1 | 8/2012 | Prodanovic |
| 2012/0215784 A1 | 8/2012 | King et al. |
| 2012/0221553 A1 | 8/2012 | Wittmer et al. |
| 2012/0226523 A1 | 9/2012 | Weiss |
| 2012/0245976 A1 | 9/2012 | Kumar et al. |
| 2012/0310661 A1 | 12/2012 | Greene |
| 2012/0323888 A1 | 12/2012 | Osann, Jr. |
| 2013/0006655 A1 | 1/2013 | Van Arkel et al. |
| 2013/0006668 A1 | 1/2013 | Van Arkel et al. |
| 2013/0016106 A1 | 1/2013 | Yip et al. |
| 2013/0054306 A1 | 2/2013 | Bhalla |
| 2013/0055145 A1 | 2/2013 | Antony et al. |
| 2013/0057551 A1 | 3/2013 | Ebert et al. |
| 2013/0096988 A1 | 4/2013 | Grossman et al. |
| 2013/0110746 A1 | 5/2013 | Ahn |
| 2013/0151453 A1 | 6/2013 | Bhanot et al. |
| 2013/0166348 A1 | 6/2013 | Scotto |
| 2013/0166480 A1 | 6/2013 | Popescu et al. |
| 2013/0185191 A1* | 7/2013 | Ganor ................ G06Q 40/02 705/39 |
| 2013/0185245 A1 | 7/2013 | Anderson |
| 2013/0185307 A1 | 7/2013 | El-Yaniv et al. |
| 2013/0218879 A1 | 8/2013 | Park et al. |
| 2013/0226318 A1 | 8/2013 | Procyk |
| 2013/0238616 A1 | 9/2013 | Rose et al. |
| 2013/0246170 A1 | 9/2013 | Gross et al. |
| 2013/0246537 A1 | 9/2013 | Gaddala |
| 2013/0246597 A1 | 9/2013 | Iizawa et al. |
| 2013/0263019 A1 | 10/2013 | Castellanos et al. |
| 2013/0268520 A1 | 10/2013 | Fisher et al. |
| 2013/0276799 A1 | 10/2013 | Davidson |
| 2013/0282696 A1 | 10/2013 | John et al. |
| 2013/0290825 A1 | 10/2013 | Arndt et al. |
| 2013/0297619 A1 | 11/2013 | Chandrasekaran et al. |
| 2013/0304770 A1 | 11/2013 | Boero et al. |
| 2013/0318604 A1 | 11/2013 | Coates et al. |
| 2014/0012796 A1 | 1/2014 | Petersen et al. |
| 2014/0040371 A1 | 2/2014 | Gurevich et al. |
| 2014/0052466 A1 | 2/2014 | DeVille et al. |
| 2014/0053091 A1 | 2/2014 | Hou et al. |
| 2014/0058754 A1 | 2/2014 | Wild |
| 2014/0058914 A1 | 2/2014 | Song et al. |
| 2014/0068487 A1 | 3/2014 | Steiger et al. |
| 2014/0081652 A1 | 3/2014 | Klindworth |
| 2014/0095509 A1 | 4/2014 | Patton |
| 2014/0108380 A1 | 4/2014 | Gotz et al. |
| 2014/0108985 A1 | 4/2014 | Scott et al. |
| 2014/0123279 A1 | 5/2014 | Bishop et al. |
| 2014/0136237 A1 | 5/2014 | Anderson et al. |
| 2014/0136285 A1 | 5/2014 | Carvalho |
| 2014/0143009 A1 | 5/2014 | Brice et al. |
| 2014/0149130 A1 | 5/2014 | Getchius |
| 2014/0156527 A1 | 6/2014 | Grigg et al. |
| 2014/0157172 A1 | 6/2014 | Peery et al. |
| 2014/0164502 A1 | 6/2014 | Khodorenko et al. |
| 2014/0189536 A1 | 7/2014 | Lange et al. |
| 2014/0189870 A1 | 7/2014 | Singla et al. |
| 2014/0195515 A1 | 7/2014 | Baker et al. |
| 2014/0214579 A1 | 7/2014 | Shen et al. |
| 2014/0222521 A1 | 8/2014 | Chait |
| 2014/0222793 A1 | 8/2014 | Sadkin et al. |
| 2014/0229554 A1 | 8/2014 | Grunin et al. |
| 2014/0244284 A1 | 8/2014 | Smith |
| 2014/0278479 A1* | 9/2014 | Wang ................ G06F 19/328 705/2 |
| 2014/0280056 A1 | 9/2014 | Kelly |
| 2014/0282160 A1 | 9/2014 | Zarpas |
| 2014/0297306 A1* | 10/2014 | Whiddon ............ G06F 19/3456 705/2 |
| 2014/0344230 A1 | 11/2014 | Krause et al. |
| 2014/0358829 A1 | 12/2014 | Hurwitz |
| 2014/0366132 A1 | 12/2014 | Stiansen et al. |
| 2015/0073929 A1 | 3/2015 | Psota et al. |
| 2015/0073954 A1 | 3/2015 | Braff |
| 2015/0081324 A1* | 3/2015 | Adjaoute ............ G06Q 40/08 705/2 |
| 2015/0095773 A1 | 4/2015 | Gonsalves et al. |

(56) References Cited

U.S. PATENT DOCUMENTS

| | | | |
|---|---|---|---|
| 2015/0100897 | A1 | 4/2015 | Sun et al. |
| 2015/0106170 | A1 | 4/2015 | Bonica |
| 2015/0106379 | A1 | 4/2015 | Elliot et al. |
| 2015/0134599 | A1 | 5/2015 | Banerjee et al. |
| 2015/0135256 | A1 | 5/2015 | Hoy et al. |
| 2015/0186821 | A1 | 7/2015 | Wang et al. |
| 2015/0187036 | A1* | 7/2015 | Wang ............ G06Q 50/22 705/2 |
| 2015/0188872 | A1 | 7/2015 | White |
| 2015/0235334 | A1* | 8/2015 | Wang ............ G06Q 40/08 705/2 |
| 2015/0242401 | A1 | 8/2015 | Liu |
| 2015/0338233 | A1 | 11/2015 | Cervelli et al. |
| 2015/0379413 | A1 | 12/2015 | Robertson et al. |
| 2016/0004764 | A1 | 1/2016 | Chakerian et al. |
| 2016/0019369 | A1* | 1/2016 | Williams ........ G16H 20/10 705/2 |
| 2016/0162456 | A1* | 6/2016 | Munro ........... G06F 16/288 704/9 |
| 2016/0180557 | A1 | 6/2016 | Yousaf et al. |
| 2016/0267224 | A1* | 9/2016 | Natarajan ....... G06N 7/005 |
| 2018/0089379 | A1* | 3/2018 | Collins ......... G06Q 10/1057 |
| 2018/0144314 | A1* | 5/2018 | Miller .......... G06Q 20/14 |

FOREIGN PATENT DOCUMENTS

| | | |
|---|---|---|
| CN | 102054015 | 5/2014 |
| DE | 102014103476 | 9/2014 |
| DE | 102014204827 | 9/2014 |
| DE | 102014204830 | 9/2014 |
| DE | 102014204834 | 9/2014 |
| EP | 2487610 | 8/2012 |
| EP | 2858018 | 4/2015 |
| EP | 2869211 | 5/2015 |
| EP | 2889814 | 7/2015 |
| EP | 2892197 | 7/2015 |
| EP | 2963595 | 1/2016 |
| EP | 2980748 | 2/2016 |
| EP | 2996053 | 3/2016 |
| EP | 3035214 | 6/2016 |
| EP | 3038002 | 6/2016 |
| EP | 3040885 | 7/2016 |
| GB | 2514239 | 11/2014 |
| WO | WO 2005/116851 | 12/2005 |
| WO | WO 2008/113059 | 9/2008 |
| WO | WO 2010/030913 | 3/2010 |
| WO | WO 2012/061162 | 5/2012 |

OTHER PUBLICATIONS

"Refresh CSS Ellipsis When Resizing Container—Stack Overflow," Jul. 31, 2013, retrieved from internet http://stackoverflow.com/questions/17964681/refresh-css-ellipsis-when-resizing-container, retrieved on May 18, 2015.

"SAP BusinessObjects Explorer Online Help," Mar. 19, 2012, retrieved on Apr. 21, 2016 http://help.sap.com/businessobject/product_guides/boexir4/en/xi4_exp_user_en.pdf.

Amnet, "5 Great Tools for Visualizing Your Twitter Followers," posted Aug. 4, 2010, http://www.amnetblog.com/component/content/article/115-5-grate-tools-for-visualizing-your-twitter-followers.html.

Appacts, "Smart Thinking for Super Apps," <http://www.appacts.com> Printed Jul. 18, 2013 in 4 pages.

Apsalar, "Data Powered Mobile Advertising," "Free Mobile App Analytics" and various analytics related screen shots <http://apsalar.com> Printed Jul. 18, 2013 in 8 pages.

Capptain—Pilot Your Apps, <http://www.capptain.com> Printed Jul. 18, 2013 in 6 pages.

Celik, Tantek, "CSS Basic User Interface Module Level 3 (CSS3 UI)," Section 8 Resizing and Overflow, Jan. 17, 2012, retrieved from internet http://www.w3.org/TR/2012/WD-css3-ui-20120117/#resizing-amp-overflow retrieved on May 18, 2015.

Chaudhuri et al., "An Overview of Business Intelligence Technology," Communications of the ACM, Aug. 2011, vol. 54, No. 8.

Cohn, et al., "Semi-supervised clustering with user feedback," Constrained Clustering: Advances in Algorithms, Theory, and Applications 4.1 (2003): 17-32.

Countly Mobile Analytics, <http://count.ly/> Printed Jul. 18, 2013 in 9 pages.

Definition "Identify", downloaded Jan. 22, 2015, 1 page.

Definition "Overlay", downloaded Jan. 22, 2015, 1 page.

Distimo—App Analytics, <http://www.distimo.com/app-analytics> Printed Jul. 18, 2013 in 5 pages.

Flurry Analytics, <http://www.flurry.com/> Printed Jul. 18, 2013 in 14 pages.

Gill et al., "Computerised Linking of Medical Records: Methodological Guidelines."

Google Analytics Official Website—Web Analytics & Reporting, <http://www.google.com/analytics.index.html> Printed Jul. 18, 2013 in 22 pages.

Gorr et al., "Crime Hot Spot Forecasting: Modeling and Comparative Evaluation", Grant 98-IJ-CX-K005, May 6, 2002, 37 pages.

Gu et al., "Record Linkage: Current Practice and Future Directions," Jan. 15, 2004, pp. 32.

Hansen et al., "Analyzing Social Media Networks with NodeXL: Insights from a Connected World", Chapter 4, pp. 53-67 and Chapter 10, pp. 143-164, published Sep. 2010.

Hua et al., "A Multi-attribute Data Structure with Parallel Bloom Filters for Network Services", HiPC 2006, LNCS 4297, pp. 277-288, 2006.

Janssen, Jan-Keno, "Wo bist'n du?—Googles Geodienst Latitude," Jan. 17, 2011, pp. 86-88, retrieved from the internet on Jul. 30, 2015 http://www.heise.de/artikel-archiv/ct/2011/03/086/@00250@/ct.11.03.086-088.pdf.

Keylines.com, "An Introduction to KeyLines and Network Visualization," Mar. 2014, <http://keylines.com/wp-content/uploads/2014/03/KeyLines-White-Paper.pdf> downloaded May 12, 2014 in 8 pages.

Keylines.com, "KeyLines Datasheet," Mar. 2014, <http://keylines.com/wp-content/uploads/2014/03/KeyLines-datasheet.pdf> downloaded May 12, 2014 in 2 pages.

Keylines.com, "Visualizing Threats: Improved Cyber Security Through Network Visualization," Apr. 2014, <http://keylines.com/wp-content/uploads/2014/04/Visualizing-Threats1.pdf> downloaded May 12, 2014 in 10 pages.

Kontagent Mobile Analytics, <http://www.kontagent.com/> Printed Jul. 18, 2013 in 9 pages.

Localytics—Mobile App Marketing & Analytics, <http://www.localytics.com/> Printed Jul. 18, 2013 in 12 pages.

Madden, Tom, "Chapter 16: The BLAST Sequence Analysis Tool," The NCBI Handbook, Oct. 2002, pp. 1-15.

Manno et al., "Introducing Collaboration in Single-user Applications through the Centralized Control Architecture," 2010, pp. 10.

Mixpanel—Mobile Analytics, <https://mixpanel.com/> Printed Jul. 18, 2013 in 13 pages.

Open Web Analytics (OWA), <http://www.openwebanalytics.com/> Printed Jul. 19, 2013 in 5 pages.

Piwik—Free Web Analytics Software. <http://piwik.org/> Printed Jul. 19, 2013 in 18 pages.

Psaltis, Andrew G., "Streaming Data—Designing the Real-Time Pipeline," Jan. 16, 2015, vol. MEAP VO3, pp. 0-12.

Sigrist, et al., "PROSITE, a Protein Domain Database for Functional Characterization and Annotation," Nucleic Acids Research, 2010, vol. 38, pp. D161-D166.

StatCounter—Free Invisible Web Tracker, Hit Counter and Web Stats, <http://statcounter.com/> Printed Jul. 19, 2013 in 17 pages.

TestFlight—Beta Testing On The Fly, <http://testflightapp.com/> Printed Jul. 18, 2013 in 3 pages.

trak.io, <http://trak.io/> printed Jul. 18, 2013 in 3 pages.

UserMetrix, <http://usermetrix.com/android-analytics> printed Jul. 18, 2013 in 3 pages.

Valentini et al., "Ensembles of Learning Machines", M. Marinaro and R. Tagliaferri (Eds.): Wirn Vietri 2002, LNCS 2486, pp. 3-20.

Vose et al., "Help File for ModelRisk Version 5," 2007, Vose Software, pp. 349-353. [Uploaded in 2 Parts].

(56) References Cited

OTHER PUBLICATIONS

Wang et al., "Research on a Clustering Data De-Duplication Mechanism Based on Bloom Filter," IEEE 2010, 5 pages.
Wikipedia, "Multimap," Jan. 1, 2013, https://en.wikipedia.org/w/index.php?title=Multimap&oldid=530800748.
Wikipedia, "Mobile Web," Jan. 23, 2015, retrieved from the internet on Mar. 15, 2016 https://en.wikipedia.org/w/index.php?title=Mobile_Web&oldid=643800164.
Windley, Phillip J., "The Live Web: Building Event-Based Connections in the Cloud," Dec. 21, 2011, pp. 10, 216.
Winkler, William E., "Bureau of the Census Statistical Research Division Record Linkage Software and Methods for Merging Administrative Lists," Statistical Research Report Series No. RR2001/03, Jul. 23, 2001, https://www.census.gov/srd/papers/pdf/rr2001-03.pdf, retrieved on Mar. 9, 2016.

\* cited by examiner

DETECTION OF MISUSE OF A BENEFIT SYSTEM

CROSS REFERENCE TO RELATED APPLICATIONS

This application claims the benefit under 35 U.S.C. § 119(e) of U.S. Provisional Application Ser. No. 62/438,185 filed Dec. 22, 2016, the content of which is incorporated by reference in its entirety into the present disclosure.

TECHNICAL FIELD

This disclosure relates to approaches for detecting misuse of a benefit system.

BACKGROUND

There are various public and private benefit systems in the society which are susceptible to misuse. Examples of such benefit systems include healthcare, public housing, food assistance, social security, senior services and community services. Certain commercial programs, such as medical and dental insurance programs, as well as auto, home and life insurance programs, are also subject to misuse. Among these benefit systems, the healthcare system, both public and private, is one or the most frequent targets for misuse which results in substantial financial loss and potentially substance abuse.

Under conventional approaches, a database may store information relating to claims made for payment (e.g., medical procedure claims, medical equipment claims, prescription claims, doctor office claims, other benefit claims, etc.). Reviewing the claims to identify potential misuse of the benefit system (e.g., fraudulent claims, prescription fraud, healthcare abuse/waste, etc.) may be time consuming and very difficult. The amount of time required and the difficulty of detecting potential frauds may lead to inaccurate and/or incomplete misuse detection.

SUMMARY

Various embodiments of the present disclosure may include systems, methods, and non-transitory computer readable media configured to automatically detect misuse of a benefit system. A database of claims may be analyzed to determine a healthcare metric. The healthcare metric may be compared to a healthcare threshold. Based on the comparison of the healthcare metric to the healthcare threshold, a first lead for investigation may be generated.

In some embodiments, the healthcare metric may characterize a relationship between one or more pharmacy events and one or more clinical events. In some embodiments, the healthcare metric may characterize an amount of opiate doses received by a patient over a period of time. In some embodiments, the healthcare metric may characterize a billing pattern of one or more healthcare providers. In some embodiments, the healthcare metric may be determined using mutual entropy.

In some embodiments, the first lead may identify one or more of patients, healthcare providers, and/or healthcare events.

In some embodiments, the systems, methods, and non-transitory computer readable media are further configured to generate a second lead for investigation based on the first lead. In some embodiments, the second lead may identify one or more of patients, healthcare providers, and/or healthcare events.

These and other features of the systems, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings of which:

DETAILED DESCRIPTION

Figure 1:
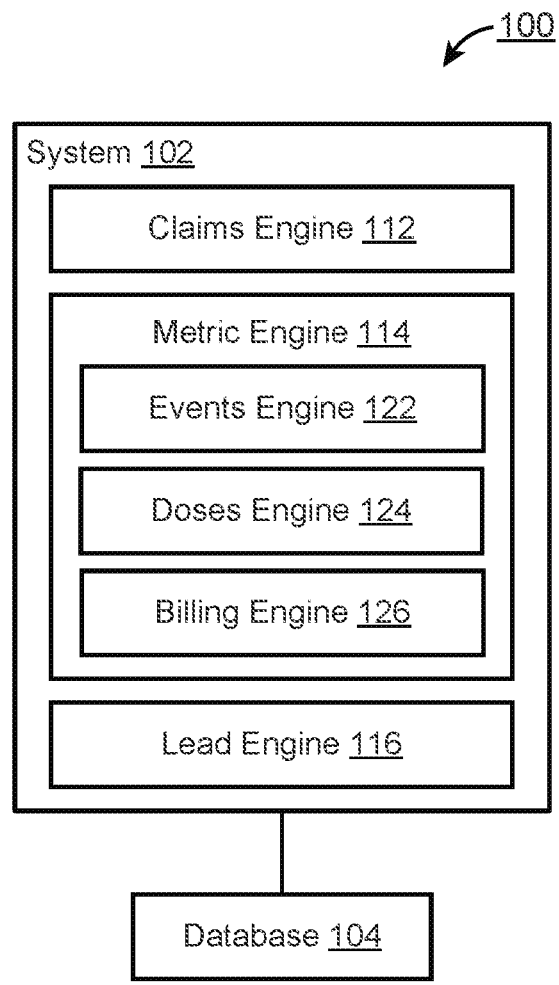
FIG. 1 illustrate an example environments for automatically detecting misuse of a benefit system, in accordance with various embodiments.

A claimed solution rooted in computer technology overcomes problems specifically arising in the realm of computer technology. In various embodiments, a computing system is configured to access and analyze a database of claims to determine leads for benefit misuse investigations. For example, in various embodiments, a computing system is configured to access and analyze a plurality of claims to determine leads for healthcare fraud investigations. Information relating to healthcare provisions (e.g., patient information, procedure performed, medical equipment used, prescription provided/filled, provider information, etc.) may be parsed from claims data to determine patterns for patients and/or healthcare providers. The patterns may be analyzed to determine specific patterns indicative of fraud/health case misuse and particular patients/healthcare providers/healthcare events may be tagged as a lead for investigation. For example, combinations of pharmacy events and clinical events may be analyzed to determine whether expected pharmacy events/clinical events are occurring. If the expected pharmacy events/clinical events are not occurring, the pharmacy events/the clinical events/patients/healthcare providers may be tagged as potential leads for healthcare misuse. As another example, the amount of opiate doses within filled prescription may be tracked to determine whether a patient fits the profile of a drug seeker and the patient/healthcare provider may be tagged as potential leads. As another example, a doctor's billing pattern may be analyzed to determine likelihood of billing fraud (e.g., upcoding) and the doctor may be tagged as a potential lead. The patterns may be analyzed using mutual entropy. Detected leads may be used to determine other leads. For example, a lead for a drug seeker may be used to track which doctors have provided prescription for the drug seeker, which may be used to determine leads for doctors engaged in prescription misuse.

The number of healthcare claims (e.g., medical procedure claims, hospital claims, medical equipment claims, prescription claims, doctor office claims, etc.) is in the range of the millions or billions per year. Individual healthcare claims may include numerous types of data, such as billing codes (e.g., procedure code, diagnosis code, etc.), patient identifier, location, service provider identifier, service date, and the like. Because databases of medical claims may contain vast amount of information, selectively mining the available information for useful purposes, such as to identify leads to potential fraudulent claims, is not a trivial task. The present disclosure enables automatic detection of misuse of a healthcare system. The techniques described herein enable automatic tagging of healthcare events, patients, and/or healthcare providers as leads for investigation.

Healthcare waste, fraud and/or abuse may be examples of healthcare misuse. As used herein, fraud refers to a scheme or artifice to defraud any healthcare program or entity or to obtain any of the money or property owned by, or under the custody or control of, any healthcare program or entity. Waste refers to the overutilization of services or other practices that, directly or indirectly, result in unnecessary costs to the healthcare system. Abuse refers to any action that may, directly or indirectly, result in one or more of unnecessary costs to the healthcare system, improper payment for services, payment for services that fail to meet professionally recognized standards of care, and/or services that are medically unnecessary.

While the disclosure is described herein with respect to fraud and fraud lead detection, this is merely for illustrative purposes and is not meant to be limiting. For example, the techniques described herein may apply to waste lead detection and/or abuse lead detection. The techniques described herein may apply to lead detection for misuse of any type of benefit systems which provide for payment/reimbursement to individuals and/or organizations for services performed/received and/or equipment provided/received.

FIG. 1 illustrates an example environment 100 for automatically detecting misuse of a benefit system, in accordance with various embodiments. The example environment 100 may include a computing system 102 and a database 104. The database 104 may include a database and/or a system of databases that receive and store data related to healthcare claims (e.g., medical procedure claims, hospital claims, medical equipment claims, prescription claims, doctor office claims, etc.) submitted by individuals and/or organizations. The data may be organized based on individuals receiving healthcare services/products, individuals/organizations providing healthcare services/products, time (e.g., a particular duration of time), insurance providers, and/or other information. Individuals receiving healthcare services/products may be referred to as patients. Individuals/organizations providing healthcare services/products may be referred to as healthcare providers. Healthcare providers may include facilities, institutions, and/or groups, such as hospitals and clinics, and/or individual practitioners such as doctors, dentists, nurses, pharmacists, and therapists. The database 104 may include supplemental information about the healthcare claims, such as individual/organization contact information, medical code information, and/or other information.

Although the database 104 is shown in FIG. 1 as a single entity, this is merely for ease of reference and is not limiting. The database 104 may represent one or more databases and/or one or more storage devices storing databases located in the same or different locations. The database 104 may be located in the same and/or different locations from the computing system 102. For example, the database 104 may be stored within the memory of the computing system 102 and/or a memory coupled to the computing system 102. The database 104 may exchange information with the computing system 102 via one or more networks.

The computing system 102 may include one or more processors and memory. The processor(s) may be configured to perform various operations by interpreting machine-readable instructions stored in the memory. As shown in FIG. 1, in various embodiments, the computing system 102 may include a claims engine 112, a metric engine 114, and a lead engine 116, and/or other engines. The metric engine 114 may include an events engine 122, a doses engine 124, and a billing engine 126. The metric engine 114 may be executed by the processor(s) of the computing system 102 to perform various operations including those described in reference to the events engine 122, the doses engine 124, and the billing engine 126. The environment may include a data store (not shown) that is accessible to the computing system 102. In some embodiments, the data store may include various databases, software packages, and/or other data that are available for download, installation, and/or execution.

In various embodiments, the claims engine 112 may be configured to access and analyze one or more databases of claims. For example, the claims engine 112 may access and analyze healthcare claims stored in the database 104. In various embodiments, the claims engine 112 may parse the information contained within the healthcare claims to identify relevant information for analysis. In some embodiments, the database 104 may include information from healthcare claims which are formatted for access by the claims engine 112. In some embodiments, the database 104 may include healthcare claims and the claims engine 112 may provide one or more of clean-up, enrichment, and/or transformation of the information within the healthcare claims for analysis. For example, the claims engine 112 may identify paid vs unpaid claims, trim unnecessary data, incorporate data from other sources (e.g., patient information, healthcare provider information, etc.) that provides context for the healthcare claims, remove duplicative information within the healthcare claims, and/or other transformation to allow the information contained within the healthcare claims to be used for misuse lead detection.

In some embodiments, the claims engine 112 may be configured to access and consolidate information contained in multiple databases of claims. The claims engine 122 may access and extract different information from different databases of claims for analysis. For example, the claims engine 112 may collect claims information from databases of claims from healthcare providers, databases of claims from insurance companies, databases of claims from publicly available information, and/or other databases.

In some embodiments, the claims engine 112 may incorporate the information obtained with the databases of claims and/or other sources (e.g., external sources) into one or more object types defined by one or more ontologies. For example, the claims engine 112 may create from the healthcare claims stored in the database 104 different objects corresponding to different healthcare participants and/or events, such as healthcare provider objects, patient objects, healthcare event objects, service objects, equipment objects, prescription objects, billing objects, and/or other objects. Packaging of information into objects may enable selective access and/or modification of the information contained within the objects. Information packaged within the objects may be accessed and/or modified during misuse lead detection.

In various embodiments, the events engine 122 may be configured determine one or more healthcare metrics based on the analysis of one or more databases of claims. The healthcare metric determined by the events engine 122 may characterize a relationship between one or more pharmacy events and one or more clinical events. A pharmacy event may refer to a medical event in which a drug is prescribed and/or a prescription for a drug is filled. For example, a pharmacy event may refer to a doctor providing a drug prescription to a patient and/or a pharmacy providing the drug to the patient. A clinical event may refer to a medical event in which a healthcare provider may assess a patient's need for pharmaceutical treatment. For example, a clinical event may include a visit to a doctor's office for a procedure that is typically accompanied by one or more prescriptions for drugs. As another example, a clinical event may include a check-up visit in which a patient's health is examined to determine whether a new prescription is required and/or a previous prescription needs to be reissued/refilled.

The healthcare metric may characterize whether one or more pharmacy events are accompanied by one or more expected clinical events. For example, certain types of drugs (e.g., Schedule II drugs) may require a patient to receive a new prescription to get a refill. Based on the analysis of database(s) of claims, the events engine 122 may determine a healthcare metric that characterizes whether a patient's filling of drugs are preceded by clinical events in which a healthcare provider would have assessed the patient's need for the drugs and provided the new prescription. For example, for a particular healthcare provider and/or a particular patient, the events engine 122 may count the number of pharmacy events (e.g., a pharmacy fills a drug prescription written by the healthcare provider) and the number of clinical events that may be associated with the pharmacy events. The events engine 122 may count the number of clinical events that occur within a certain period of time before and/or after the pharmacy event.

A healthcare provider whose practice includes an expected number of clinical events associated with pharmacy events may be scored with a satisfactory healthcare metric (e.g., high or low score). A healthcare provider whose practice includes a lower than expected number of clinical events associated with pharmacy events may be scored with an unsatisfactory healthcare metric (e.g., low or high score). A healthcare provider whose practice includes a lower than expected number of clinical events associated with pharmacy events may be practicing poor standard of care (e.g., bad pain management—not meeting with patients to whom the healthcare provider is providing prescriptions). A healthcare provider whose clinical events are not occurring within a certain time duration of the pharmacy events may be practicing poor standard of care.

A patient who is associated with an expected number of clinical events for pharmacy events may be scored with a satisfactory healthcare metric (e.g., high or low score). A patient who is associated with a lower than expected number of clinical events for pharmacy events may be scored with an unsatisfactory healthcare metric (e.g., low or high score). A patient who is associated with a lower than expected number of clinical events for pharmacy events may have a healthcare provider practicing bad pain management (e.g., not meeting with patients to whom the healthcare provider is providing prescriptions) and/or may be falsifying prescriptions.

In various embodiments, the doses engine 124 may be configured to determine one or more healthcare metrics based on the analysis of one or more databases of claims. The healthcare metric determined by the doses engine 124 may characterize the amount of opiate doses received by a patient over one or more periods of time. The doses engine 124 may leverage information within the database of claims to determine the amount of opiate doses received by a patent. The doses engine 124 may convert the amount of opiate doses received by the patient into a morphine equivalent. For example, different types of drugs may be associated with different levels of morphine, and information about the types and amounts of drugs received by a patient may be converted into a morphine equivalent. The healthcare metric may characterize the amount of opiate doses received by a patient based on the morphine equivalent received by the patient. In some embodiment, the opiate doses may be aggregated on a periodic basis (e.g., daily, weekly, monthly, yearly, etc.). High amounts of morphine equivalent for a patient for a given period of time may indicate that the patient may be a drug seeker. In some embodiments, the healthcare metric for the individual patients may be aggregated to determine the healthcare metric for a healthcare provider. High score for a healthcare provider may indicate that the healthcare provider potentially provides prescriptions for one or more drug seeking patients.

In some embodiments, the healthcare metric determined by the doses engine 124 may be adjusted based on patient information. For example, the healthcare metric may be adjusted based on the size of the patient so that the variance of amount of opiate doses received by the patient based on the size of the patient is factored into the healthcare metric. As another example, the healthcare metric may be adjusted based on the patient's current health condition (e.g., diagnosed diseases) so that the variance of amount of opiate doses received by the patient due to the patient's health condition is factored into the healthcare metric. For instance, a patient diagnosed with cancer may be expected to receive higher amounts of opiate doses than a patient diagnosed with a cold.

In various embodiments, the billing engine 126 may be configured to determine one or more healthcare metrics based on the analysis of one or more databases of claims. The healthcare metric determined by the billing engine 126 may be characterized by a billing pattern of one or more healthcare providers. The healthcare metric determined by the billing engine 126 may indicate whether the healthcare providers may be engaged in fraudulent billing practices. For example, the healthcare metric may indicate whether the healthcare providers are engaged in upcoding (e.g., using a more expensive code for payment) and/or other practices to receive money for medical services/equipment that was not provided to patients.

In some embodiments, the billing engine 126 may use mutual entropy to determine whether the healthcare providers are engaging in fraudulent billing practices. The billing engine 126 may use mutual entropy to determine mutual information between the healthcare providers' billings and the patients seen by the healthcare providers. The mutual information may indicate whether the healthcare providers' billings (indicating the medical services performed and/or medical equipment used/provided, etc.) are independent or dependent on the patients seen by the healthcare providers. Mutual entropy may determine whether there is a connection between a particular patient/visit and the treatment provided/billed by the healthcare provider. Mutual entropy may determine whether there is a connection between a patient and the type of treatment received by the patient. Healthcare providers that bill for the same/similar types of treatment regardless of the patient identity/visit may be engaged in fraudulent billing practices. Healthcare providers with billing entries that are tailored to different patients/visits may receive a higher healthcare metric than healthcare providers with billing entries that include same/similar claims across different patients/visits. For example, a doctor who bills for a urine test for every patient may be scored with a lower healthcare metric than a doctor who bills a urine test for a subgroup of patients. A healthcare provider with a low healthcare metric determined based on mutual entropy may be engaged in "cookie-cutter billing," where the healthcare providers bills for the same/similar treatment regardless of the patient they see and/or the type of visit.

Calculation of healthcare metric based on mutual entropy may be grouped by specialty/classes of healthcare providers. For example, a certain specialty (e.g., radiologists) may use a smaller subset of codes for billing than another specialty (e.g., family medicine). Calculating mutual entropy across different specialties may result in healthcare providers in specialties with smaller number of billing codes having lower healthcare metrics than healthcare provider in specialties with larger number of billing codes. Grouping the calculation of mutual entropy by specialty/classes of healthcare providers may enable comparison of billing practices among similar types of healthcare providers.

In some embodiments, the billing engine 126 may weigh different parameters for the mutual entropy calculation differently. For example, the billing engine 126 may focus on (weigh more heavily) certain kinds of treatments, equipment, and/or specialties that are more prone to being subject of fraudulent billing practices. As another example, the billing engine 126 may discard (weigh less heavily) most common codes used by healthcare providers (e.g., codes expected to be billed for every/most patients). Such codes may be of such high volume that they may skew the mutual entropy calculation and hide misuse of less common codes. Disregarding such codes may allow the mutual entropy calculation (and the healthcare metric) to reflect the misuse of less common codes.

In some embodiments, the billing engine 126 may determine mutual entropy by different time periods (e.g., per visit, per a number of visits, daily, weekly, monthly, yearly, etc.), by the healthcare provider's specialty, and/or by specific codes (e.g., CPT code) for different patients/healthcare providers. For example, determining mutual entropy based on treatments provided to patients over a three month period may provide different indication of the healthcare provider's billing practices than determining mutual entropy based on treatments provided to patients over a single visit.

In some embodiments, the billing engine 126 may use billing trends to determine whether the healthcare providers are engaging in fraudulent billing practices. The billing engine 126 may analyze the billing entries of healthcare providers to determine if the healthcare providers are increasing the use of more expensive billing codes over time (e.g., the healthcare providers are starting to upcode, etc.). The billing engine 126 may analyze the billing entries to detect patterns of billing independent of patients seen by the healthcare providers. For example, the healthcare providers may bill one or more particular codes at a regular interval (e.g., a healthcare provider may bill a particular code every thirty days regardless of the identities and/or the number of patients seen by the healthcare provider). The healthcare metric may characterize the pattern detected by the billing engine 126.

The billing engine 126 may analyze the billing entries to determine levels and/or periodicity of billing that are independent of external factors. For example, healthcare providers may, on average, experience fluctuations on the number of patients seen/number of billing entries/types of billing entries based on the time of the year and/or weather conditions. The billing engine 126 may analyze the billing entries to determine whether particular healthcare providers do not experience fluctuations in billing experienced by other healthcare providers (e.g., a particular healthcare provider's billing is not affected by changes in weather, temperature, humidity, etc.).

In some embodiments, the billing engine 126 may access information about external factors to identify periods of time when the billings of the healthcare providers may fluctuate. For example, the billing engine 126 may access weather information to determine periods when healthcare providers' billings are expected to decrease. The billing engine 126 may analyze the billing entries to determine which healthcare providers' billing entries stayed level or increased during those periods.

In some embodiments, the billing engine 126 may analyze billing entries to determine when the providers and/or patients are engaging in unlikely/impossible activities. For example, the billing engine 126 may analyze billing entries to determine when a particular provider has billed more than 24 hours' worth of codes during a single day (billing an "impossible day"). As another example, the billing engine 126 may analyze billing entries to determine when a particular patient's multiple visits to a healthcare provider and/or visits to multiple healthcare providers in a set amount of time may be of suspect. For example, a particular patient may have visited more healthcare providers/had more visits to a healthcare provider than would be likely during a given time period (e.g., a day). As another example, a particular patient may have visited healthcare providers located far from each other such that the timing of the visit (e.g., visited during the same day) is unlikely. Such unlikely visits by a patient may indicate that one or more healthcare providers are engaging in medical identify theft (using patient information to bill for patients not seen).

In some embodiments, one or more healthcare metrics may be determined using the systems/methods/non-transitory computer readable medium as disclosed in application Ser. No. 15/181,712, "FRAUD LEAD DETECTION SYSTEM FOR EFFICIENTLY PROCESSING DATABASE-STORED DATA AND AUTOMATICALLY GENERATING NATURAL LANGUAGE EXPLANATORY INFORMATION OF SYSTEM RESULTS FOR DISPLAY IN INTERACTIVE USER INTERFACES," filed on Jun. 14, 2016, which is hereby incorporated by reference in its entirety.

In various embodiments, the lead engine 116 may be configured to compare a healthcare metric to a healthcare threshold and generate one or more leads for investigation based on the comparison. A healthcare threshold may include a static value and/or a dynamic value to which the healthcare metric may be compared. A healthcare threshold may be set manually (e.g., by a user) and/or may be set automatically. For example, for different types of healthcare metrics (e.g., determined based on pharmacy events and clinical events, opiate doses, billing pattern, mutual entropy, etc.), a user may manually set the healthcare threshold such that healthcare metrics that meet, exceed, or fall below the healthcare threshold are used to generate leads for investigation. As another example, for different types of healthcare metrics, the lead engine 116 may determine the healthcare threshold based on aggregation of healthcare metrics such that the healthcare threshold represents a certain statistical deviation from the aggregated healthcare metrics.

For example, for healthcare metrics of healthcare providers and/or patients determined based on pharmacy events and clinical events, the healthcare threshold may be determined based on an expected numbers of pharmacy events associated with clinical events (e.g., ratio of numbers of pharmacy events to numbers of associated clinical events) and/or based on the duration between the occurrences of pharmacy events and associated clinical events (e.g., does a clinical event occur within a certain duration before and/or after a pharmacy event; how many clinical events occur within a certain duration before and/or after pharmacy events). Based on the healthcare metric of the healthcare providers and/or the patients not satisfying the healthcare threshold, the lead engine 116 may identify as leads for investigation one or more of the corresponding healthcare providers, the patients, and/or the healthcare events (e.g., clinical event, pharmacy event, etc.).

As another example, for healthcare metrics of healthcare providers and/or patients determined based on opiate doses received by patients, the healthcare threshold may be determined based on a certain amount of opiate doses/morphine equivalent. Based on the healthcare metric of the healthcare providers and/or the patients not satisfying the healthcare threshold, the lead engine 116 may identify as leads for investigation one or more of the corresponding healthcare providers, the patients, and/or the healthcare events (e.g., clinical event, pharmacy event, etc.).

As another example, for healthcare metrics of healthcare providers determined based on mutual entropy, the healthcare threshold may be determined based on a value indicating a certain dependence/independence between the healthcare providers' billings and the patients seen by the healthcare providers. Based on the healthcare metric of the healthcare providers not satisfying the healthcare threshold, the lead engine 116 may identify as leads for investigation one or more of the corresponding healthcare providers.

As another example, for healthcare metrics of healthcare providers determined based on billing trends, the healthcare threshold may be determined based on a value indicating a certain trend/pattern of billing. For example, the healthcare threshold may be set based on a maximum amount of billings and/or increase in the use of more expensive billing codes for a set duration of time, based on the level/periodicity of billings that are independent of external factors, and/or based on the number/level of unlikely/impossible activities reflected by the claims. Based on the healthcare metric of the healthcare providers not satisfying the healthcare threshold, the lead engine 116 may identify as leads for investigation one or more of the corresponding healthcare providers.

In some embodiments, the lead engine 116 may use the comparison of healthcare metrics to healthcare thresholds as one among multiple factors for generating leads for investigation. The lead engine 116 may review other factors when a healthcare metric does not satisfy the healthcare threshold. For example, with respect to healthcare metrics of healthcare providers and/or patients determined based on opiate doses received by patients, other factors may include whether a patient has a recorded history of displaying characteristics/behaviors of a drug dependent person (e.g., frequent visits to the emergency room, seeing many different doctors, visiting many different pharmacies, etc.). The lead engine 116 may use a classifier to return a probability, based on the comparison of the healthcare metric to healthcare thresholds and other factors, that a patient is a drug seeker.

As another example, with respect to healthcare metrics of healthcare providers determined based on mutual entropy, other factors may include total billing and/or total volume of services/products provided by the healthcare providers. The lead engine 116 may identify as a lead one or more healthcare providers whose healthcare metric does not satisfy the healthcare threshold and whose totally billing/volume is higher than others (e.g., top bills, top volumes).

In some embodiments, the lead engine 116 may use multiple comparisons between healthcare metrics and healthcare thresholds to generate leads for investigation. For example, the lead engine 116 may identify patients whose healthcare metrics (e.g., determined based on amount of opiate doses and/or other factors) indicate that the patients may be drug seekers and identify healthcare providers whose healthcare metrics (e.g., determined based on clinical events and pharmacy events) indicate the healthcare providers may be practicing bad pain management. The overlap between the identified patients and the identified healthcare providers (including healthcare providers potentially practicing bad pain management and seeing potentially drug seeking patients) may be identified as leads for investigation.

In various embodiments, the lead engine 116 is configured to generate additional leads for investigation based on previously generated leads. For example, based on a lead identifying healthcare providers providing unnecessary amounts of drugs, the lead engine 116 may generate leads for investigations patients who see the identified healthcare providers. The patients who were prescribed higher amounts opiate doses and/or displaying characteristics/behaviors of drug seeker may be identified as leads. As another example, a lead identifying a patient as a potential drug seeker may be used to track which healthcare providers have provided prescription for the patient. A healthcare providers who see and/or provide prescriptions for more patients identified as potential drug seeker may be identified as leads. Backtracking leads of healthcare providers may enable construction of a network model that provides a view of how tightly connected the healthcare providers are through their patients. For example, the network model may indicate which healthcare providers may be connected in their misuse of the healthcare system and/or may indicate which healthcare providers a drug seeking patient may turn to if one of the identified healthcare providers is shut down.

In some embodiments, one or more healthcare thresholds may be determined, and/or one or more leads may be identified and/or reported using the systems/methods/non-transitory computer readable medium as disclosed in application Ser. No. 15/181,712, "FRAUD LEAD DETECTION SYSTEM FOR EFFICIENTLY PROCESSING DATABASE-STORED DATA AND AUTOMATICALLY GENERATING NATURAL LANGUAGE EXPLANATORY INFORMATION OF SYSTEM RESULTS FOR DISPLAY IN INTERACTIVE USER INTERFACES," filed on Jun. 14, 2016, incorporated supra.

Figure 2:
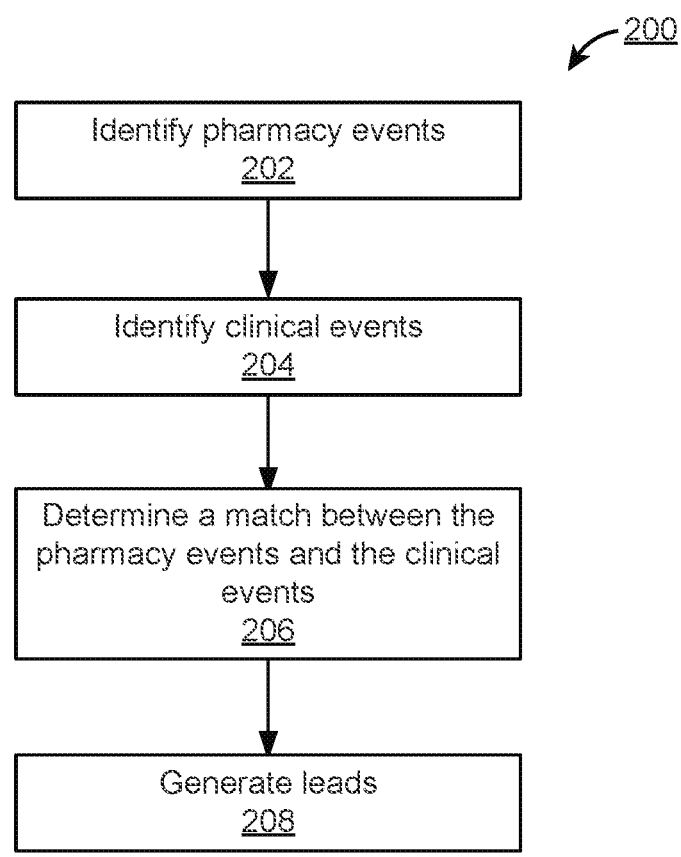
FIG. 2 illustrates an exemplary process for generating leads based on pharmacy events and clinical events, in accordance with various embodiments.

FIG. 2 illustrates an exemplary process 200 for generating leads based on pharmacy events and clinical event. The process 200 may be implemented in various environments, including, for example, the environment of FIG. 1. At block 202, one or more pharmacy events for a patient/healthcare provider may be identified from one or more databases of claims. At block 204, one or more clinical events for a patient/healthcare provider may be identified from one or more databases of claims. At block 206, one or more matches between the pharmacy event(s) and the clinical event(s) may be determined. A match between the pharmacy event(s) and the clinical event(s) may exist when the timing of the pharmacy event(s) and the clinical event(s) indicate that the pharmacy event(s) occurred as a result of the clinical event(s). At block 208, one or more leads may be generated based on the matches between the pharmacy event(s) and the clinical event(s). Lead(s) may be generated when the matches between the pharmacy event(s) and the clinical event(s) indicate less than a desired number/timing of clinical events for pharmacy events (e.g., a patient getting prescriptions filled without seeing a doctor, a doctor writing prescriptions for a patient without seeing the patients, etc.).

Figure 3:
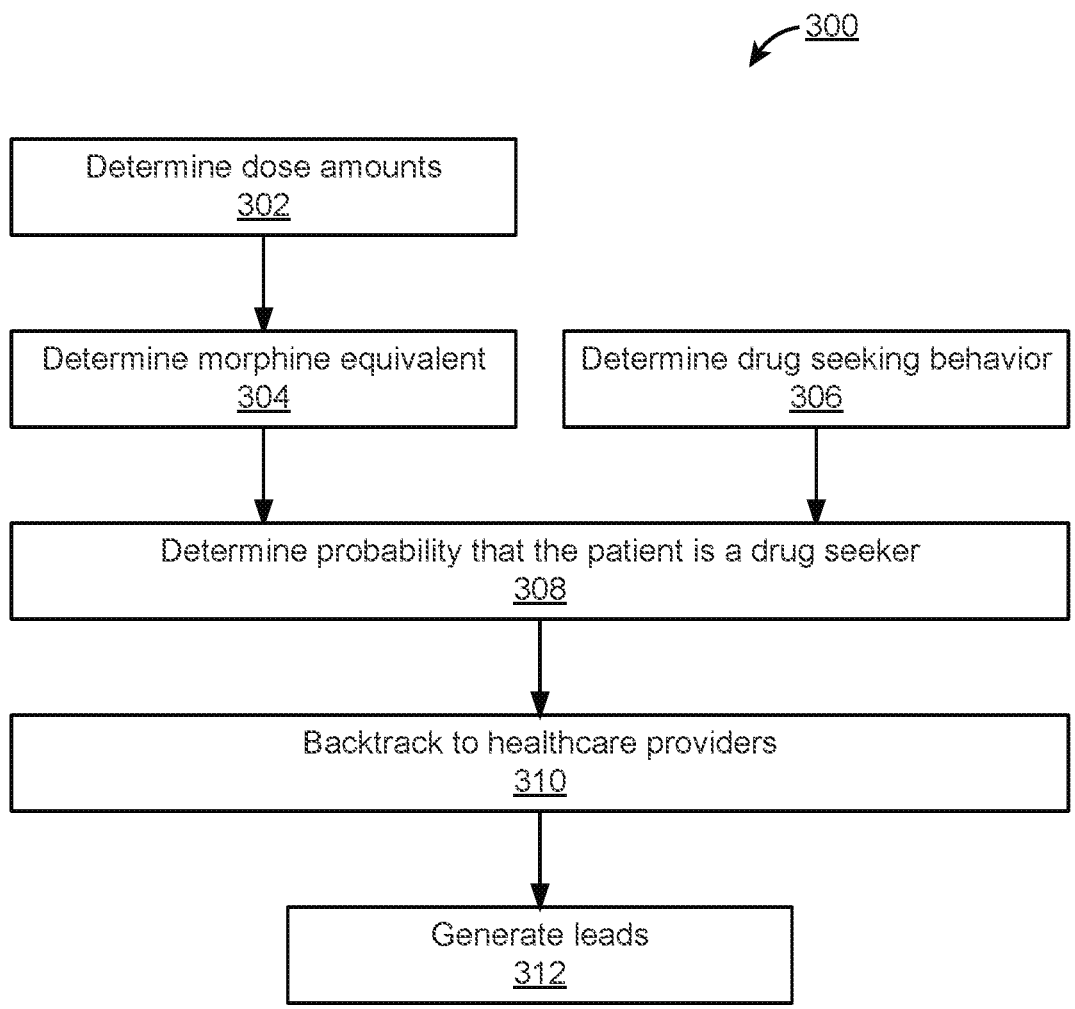
FIG. 3 illustrates an exemplary process for generating leads based on opiate doses, in accordance with various embodiments.

FIG. 3 illustrates an exemplary process 300 for generating leads based on opiate doses. The process 300 may be implemented in various environments, including, for example, the environment of FIG. 1. At block 302, the dose amounts for a patient may be determined. At block 304, the morphine equivalent of the dose amounts may be determined. At block 306, one or more drug seeking behaviors/characteristics of the patient may be determined. At block 308, the probability that the patient is a drug seeker may be determined based on the morphine equivalent of the dose amounts and the drug seeking behaviors/characteristics of the patients. At block 310, identifies of one or more potentially drug-seeking patients may be used to backtrack to the healthcare providers who provided prescription to these patients. At block 312, one or more leads may be generated based on the identified patients and/or identified healthcare providers.

Figure 4:
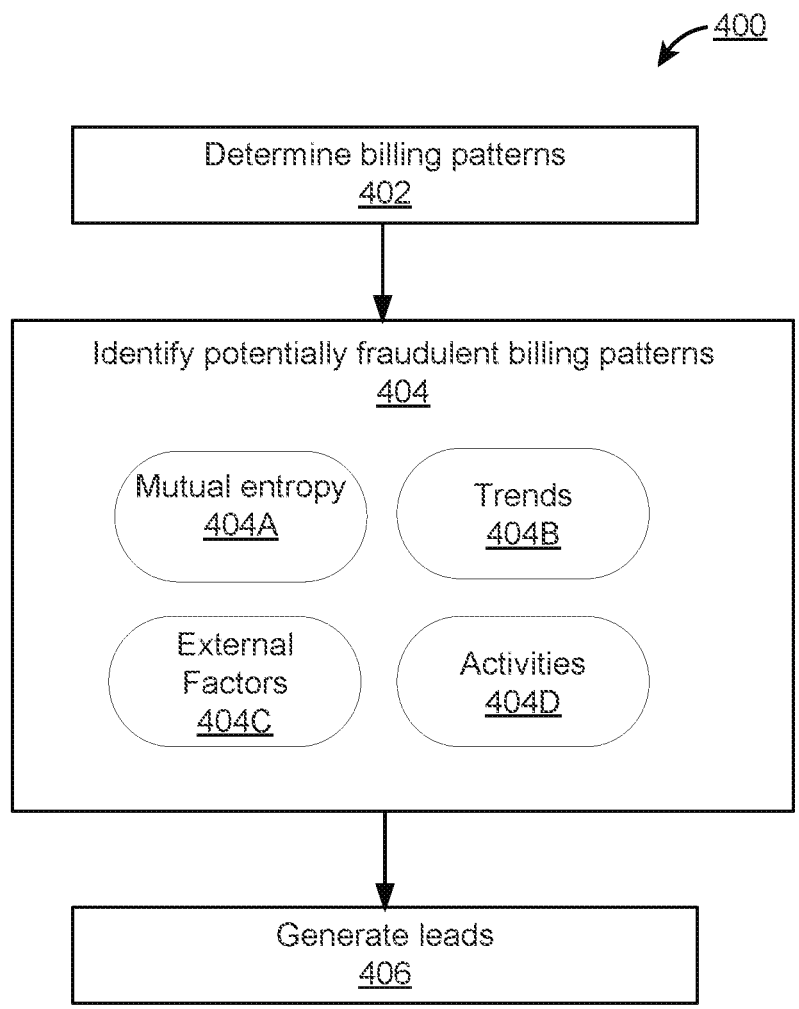
FIG. 4 illustrates an exemplary process for generating leads based on billing patterns, in accordance with various embodiments.

FIG. 4 illustrates an exemplary process 400 for generating leads based on billing patterns. The process 400 may be implemented in various environments, including, for example, the environment of FIG. 1. At block 402, billing patterns of one or more healthcare providers may be determined. At block 404, potentially fraudulent billing patterns may be identified. In some embodiments, identifying potentially fraudulent billing patterns may include the use of mutual entropy 404A to determine the dependence/independence between the healthcare providers' billings and the patients seen by the healthcare provider. In some embodiments, identifying potentially fraudulent billing patterns may include the detection of trends 404B that indicate upcoding. In some embodiments, identifying potentially fraudulent billing patterns may include determining the influence/lack of influence of external factors 404C on billing patterns. In some embodiments, identifying potentially fraudulent billing patterns may include detecting unlikely/impossible activities 404D. At block 406, one or more leads may be generated based on the potentially fraudulent billing patterns.

Figure 5:
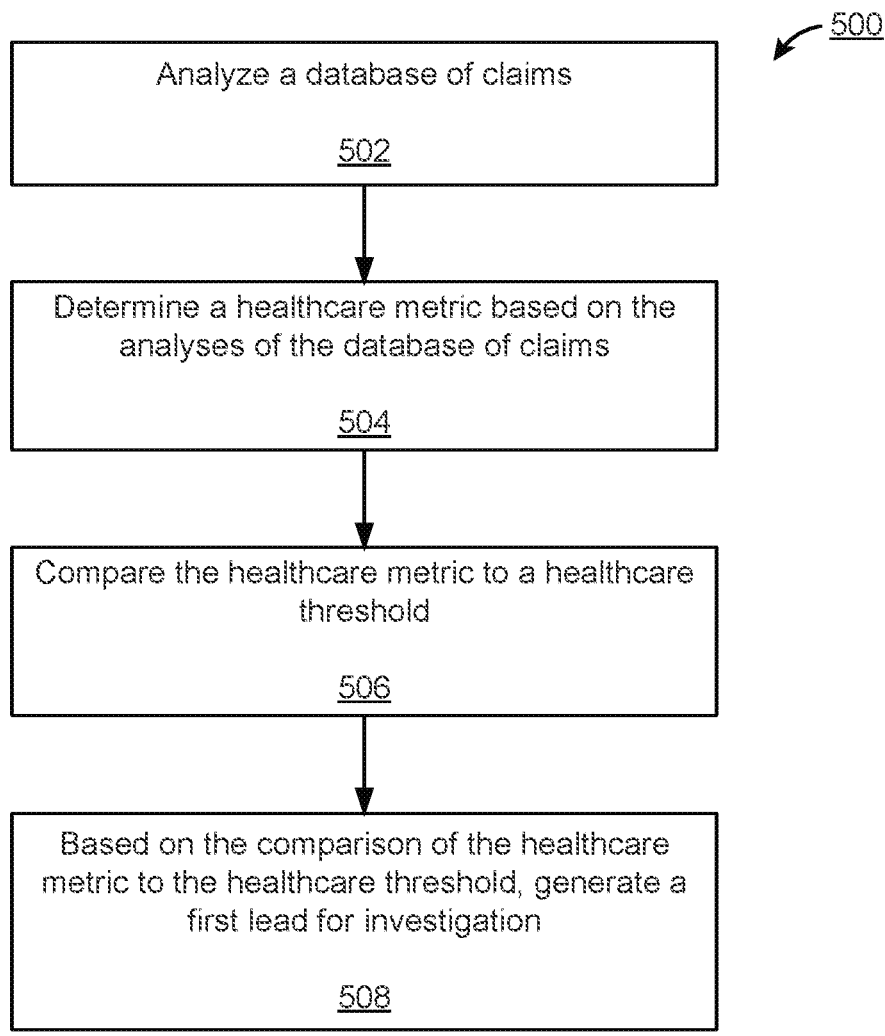
FIG. 5 illustrates a flowchart of an example method, in accordance with various embodiments.

FIG. 5 illustrates a flowchart of an example method 500, according to various embodiments of the present disclosure. The method 500 may be implemented in various environments including, for example, the environment 100 of FIG. 1. The operations of method 500 presented below are intended to be illustrative. Depending on the implementation, the example method 500 may include additional, fewer, or alternative steps performed in various orders or in parallel. The example method 500 may be implemented in various computing systems or devices including one or more processors.

At block 502, a database of claims may be analyzed. At block 504, a healthcare metric may be determined based on the analyses of the database of claims. At block 506, the healthcare metric may be compared to a healthcare threshold. At block 508, based on the comparison of the healthcare metric to the healthcare threshold, a first lead for investigation may be generated.

Hardware Implementation

The techniques described herein are implemented by one or more special-purpose computing devices. The special-purpose computing devices may be hard-wired to perform the techniques, or may include circuitry or digital electronic devices such as one or more application-specific integrated circuits (ASICs) or field programmable gate arrays (FPGAs) that are persistently programmed to perform the techniques, or may include one or more hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 6:
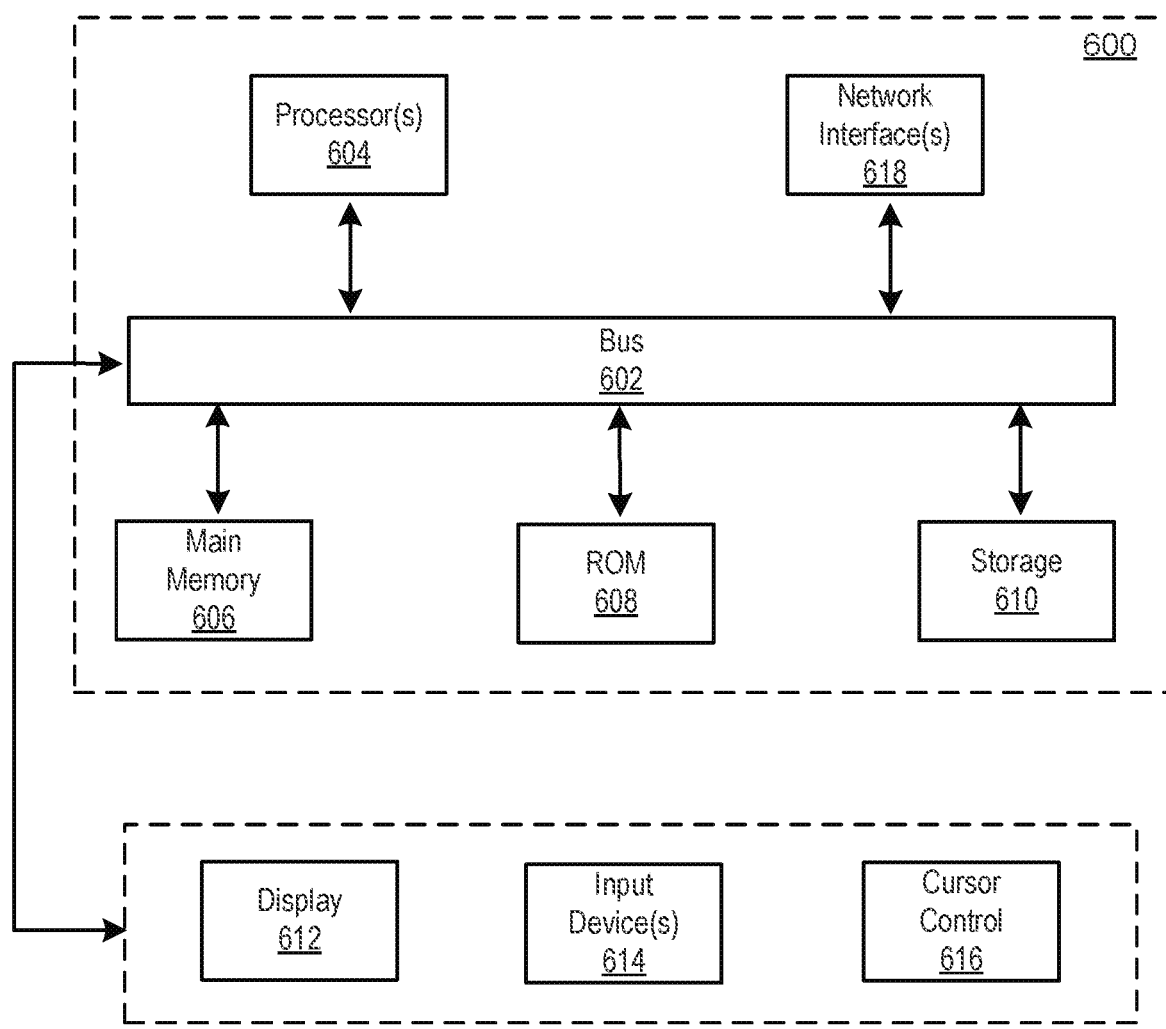
FIG. 6 illustrates a block diagram of an example computer system in which any of the embodiments described herein may be implemented.

FIG. 6 is a block diagram that illustrates a computer system 600 upon which any of the embodiments described herein may be implemented. The computer system 600 includes a bus 602 or other communication mechanism for communicating information, one or more hardware processors 604 coupled with bus 602 for processing information. Hardware processor(s) 604 may be, for example, one or more general purpose microprocessors.

The computer system 600 also includes a main memory 606, such as a random access memory (RAM), cache and/or other dynamic storage devices, coupled to bus 602 for storing information and instructions to be executed by processor 604. Main memory 606 also may be used for storing temporary variables or other intermediate information during execution of instructions to be executed by processor 604. Such instructions, when stored in storage media accessible to processor 604, render computer system 600 into a special-purpose machine that is customized to perform the operations specified in the instructions.

The computer system 600 further includes a read only memory (ROM) 608 or other static storage device coupled to bus 602 for storing static information and instructions for processor 604. A storage device 610, such as a magnetic disk, optical disk, or USB thumb drive (Flash drive), etc., is provided and coupled to bus 602 for storing information and instructions.

The computer system 600 may be coupled via bus 602 to a display 612, such as a cathode ray tube (CRT) or LCD display (or touch screen), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

The computing system 600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor(s) 604 executing one or more sequences of one or more instructions contained in main memory 606. Such instructions may be read into main memory 606 from another storage medium, such as storage device 610. Execution of the sequences of instructions contained in main memory 606 causes processor(s) 604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 610. Volatile media includes dynamic memory, such as main memory 606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 602. Transmission media can also take the form of acoustic or light waves, such as those generated during radio-wave and infra-red data communications.

Various forms of media may be involved in carrying one or more sequences of one or more instructions to processor 604 for execution. For example, the instructions may initially be carried on a magnetic disk or solid state drive of a remote computer. The remote computer can load the instructions into its dynamic memory and send the instructions over a telephone line using a modem. A modem local to computer system 600 can receive the data on the telephone line and use an infra-red transmitter to convert the data to an infra-red signal. An infra-red detector can receive the data carried in the infra-red signal and appropriate circuitry can place the data on bus 602. Bus 602 carries the data to main memory 606, from which processor 604 retrieves and executes the instructions. The instructions received by main memory 606 may retrieves and executes the instructions. The instructions received by main memory 606 may optionally be stored on storage device 610 either before or after execution by processor 604.

The computer system 600 also includes a communication interface 618 coupled to bus 602. Communication interface 618 provides a two-way data communication coupling to one or more network links that are connected to one or more local networks. For example, communication interface 618 may be an integrated services digital network (ISDN) card, cable modem, satellite modem, or a modem to provide a data communication connection to a corresponding type of telephone line. As another example, communication interface 618 may be a local area network (LAN) card to provide a data communication connection to a compatible LAN (or WAN component to communicated with a WAN). Wireless links may also be implemented. In any such implementation, communication interface 618 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet". Local network and Internet both use electrical, electromagnetic or optical signals that carry digital data streams. The signals through the various networks and the signals on network link and through communication interface 618, which carry the digital data to and from computer system 600, are example forms of transmission media.

The computer system 600 can send messages and receive data, including program code, through the network(s), network link and communication interface 618. In the Internet example, a server might transmit a requested code for an application program through the Internet, the ISP, the local network and the communication interface 618.

The received code may be executed by processor 604 as it is received, and/or stored in storage device 610, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Engines, Components, and Logic

Certain embodiments are described herein as including logic or a number of components, engines, or mechanisms. Engines may constitute either software engines (e.g., code embodied on a machine-readable medium) or hardware engines. A "hardware engine" is a tangible unit capable of performing certain operations and may be configured or arranged in a certain physical manner. In various example embodiments, one or more computer systems (e.g., a standalone computer system, a client computer system, or a server computer system) or one or more hardware engines of a computer system (e.g., a processor or a group of processors) may be configured by software (e.g., an application or application portion) as a hardware engine that operates to perform certain operations as described herein.

In some embodiments, a hardware engine may be implemented mechanically, electronically, or any suitable combination thereof. For example, a hardware engine may include dedicated circuitry or logic that is permanently configured to perform certain operations. For example, a hardware engine may be a special-purpose processor, such as a Field-Programmable Gate Array (FPGA) or an Application Specific Integrated Circuit (ASIC). A hardware engine may also include programmable logic or circuitry that is temporarily configured by software to perform certain operations. For example, a hardware engine may include software executed by a general-purpose processor or other programmable processor. Once configured by such software, hardware engines become specific machines (or specific components of a machine) uniquely tailored to perform the configured functions and are no longer general-purpose processors. It will be appreciated that the decision to implement a hardware engine mechanically, in dedicated and permanently configured circuitry, or in temporarily configured circuitry (e.g., configured by software) may be driven by cost and time considerations.

Accordingly, the phrase "hardware engine" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented engine" refers to a hardware engine. Considering embodiments in which hardware engines are temporarily configured (e.g., programmed), each of the hardware engines need not be configured or instantiated at any one instance in time. For example, where a hardware engine comprises a general-purpose processor configured by software to become a special-purpose processor, the general-purpose processor may be configured as respectively different special-purpose processors (e.g., comprising different hardware engines) at different times. Software accordingly configures a particular processor or processors, for example, to constitute a particular hardware engine at one instance of time and to constitute a different hardware engine at a different instance of time.

Hardware engines can provide information to, and receive information from, other hardware engines. Accordingly, the described hardware engines may be regarded as being communicatively coupled. Where multiple hardware engines exist contemporaneously, communications may be achieved through signal transmission (e.g., over appropriate circuits and buses) between or among two or more of the hardware engines. In embodiments in which multiple hardware engines are configured or instantiated at different times, communications between such hardware engines may be achieved, for example, through the storage and retrieval of information in memory structures to which the multiple hardware engines have access. For example, one hardware engine may perform an operation and store the output of that operation in a memory device to which it is communicatively coupled. A further hardware engine may then, at a later time, access the memory device to retrieve and process the stored output. Hardware engines may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein. As used herein, "processor-implemented engine" refers to a hardware engine implemented using one or more processors.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

It will be appreciated that an "engine," "system," "data store," and/or "database" may comprise software, hardware, firmware, and/or circuitry. In one example, one or more software programs comprising instructions capable of being executable by a processor may perform one or more of the functions of the engines, data stores, databases, or systems described herein. In another example, circuitry may perform the same or similar functions. Alternative embodiments may comprise more, less, or functionally equivalent engines, systems, data stores, or databases, and still be within the scope of present embodiments. For example, the functionality of the various systems, engines, data stores, and/or databases may be combined or divided differently.

"Open source" software is defined herein to be source code that allows distribution as source code as well as compiled form, with a well-publicized and indexed means of obtaining the source, optionally with a license that allows modifications and derived works.

The data stores described herein may be any suitable structure (e.g., an active database, a relational database, a self-referential database, a table, a matrix, an array, a flat file, a documented-oriented storage system, a non-relational NoSQL system, and the like), and may be cloud-based or otherwise.

As used herein, the term "or" may be construed in either an inclusive or exclusive sense. Moreover, plural instances may be provided for resources, operations, or structures described herein as a single instance. Additionally, boundaries between various resources, operations, engines, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system comprising:
one or more processors; and
a memory storing instructions that, when executed by the one or more processors, in conjunction with a particular machine learning model for a subset of the instructions, cause the system to perform:
analyzing a dynamically updating database of claims;
determining a healthcare metric based on the analyses of the database of claims, the healthcare metric characterizing a relationship between one or more pharmacy events and one or more clinical events;
determining an expected pattern of the healthcare metric in relation to a factor;
comparing, to the expected pattern, an actual pattern of the healthcare metric in relation to the factor;
based on the comparison of the actual pattern of the healthcare metric to the expected pattern, automatically determining a potential source of fraud;
determining a second potential source of fraud based on the identified potential source of fraud;
in response to the potential source of fraud or the second potential source of fraud being shut down, determining a backup potential source of fraud, the determining the potential source of fraud, the second potential source of fraud, and the backup potential source of fraud using one or more machine learning models, the one or more machine learning models comprising the particular machine learning model;
determining a similarity between the potential source of fraud, the second potential source of fraud, and the backup potential source of fraud with a known instance of fraud;
generating, using natural language processing, an explanation indicating:
the similarity between the potential source of fraud, the second potential source of fraud, and the backup potential source of fraud with the known instance of fraud; and
the particular machine learning model, which has a highest contribution in determining the potential source of fraud, the second potential source of fraud and the backup potential source of fraud;
appending the explanation and the reasoning to a presentation of the potential source of fraud, the second potential source of fraud, and the backup potential source of fraud;
selecting, from among known outcomes of analyses in which veracities of previous potential sources of fraud have been determined, training datasets to train the particular machine learning model, the selecting being based on scenarios associated with the known outcomes that comprise highest uncertainty levels in the particular machine learning model and which increase an accuracy of the particular machine learning model by highest amounts following the training, wherein the training datasets comprise a first training dataset of sources verified to be fraudulent and a second training dataset of sources verified to be non-fraudulent; and
iteratively training the particular machine learning model using the first training dataset and the second training dataset.

2. The system of claim 1, wherein determining the healthcare metric includes determining whether the one or more pharmacy events are accompanied by the one or more clinical events.

3. The system of claim 2, wherein determining whether the one or more pharmacy events are accompanied by the one or more clinical events includes determining respective durations between occurrences of the one or more pharmacy events and the one or more clinical events.

4. The system of claim 1, wherein the expected pattern is characterized by an expected number of clinical events associated with the one or more pharmacy events.

5. The system of claim 1, wherein the one or more pharmacy events include one or more medical events in which a drug is prescribed or a prescription for the drug is filled.

6. The system of claim 1, wherein the one or more clinical events include one or more medical events in which a healthcare provider assesses a patient's need for pharmaceutical treatment.

7. The system of claim 1, wherein the factor is a weather condition.

8. The system of claim 7, wherein the potential source of fraud identifies one or more of patients, healthcare providers, or healthcare events, and the second potential source of fraud identifies one or more of patients, healthcare providers, and/or healthcare events.

9. The system of claim 1, wherein the iteratively training of the particular machine learning model comprises:
calculating new weights of signals associated with the particular machine learning model; and
detecting a known instance of fraud that was undetected by the trained particular machine learning model; and
incorporating the known instance of fraud into the trained particular machine learning model.

10. The system of claim 1, wherein the instructions further cause the system to perform:
in response to verifying the potential source of fraud, the second potential source of fraud, or the backup potential source of fraud, providing a treatment to a patient.

11. A system comprising:
one or more processors; and
a memory storing instructions that, when executed by the one or more processors, in conjunction with a particular machine learning model for a subset of the instructions, cause the system to perform:
analyzing a database of claims;
determining a healthcare metric based on the analyses of the database of claims, the healthcare metric determined based on an amount of opiate doses received by a patient over a period of time;
determining an expected pattern of the healthcare metric in relation to a factor;
comparing, to the expected pattern, an actual pattern of the healthcare metric in relation to the factor;
based on the comparison of the actual pattern of the healthcare metric to the expected pattern, automatically determining a potential source of fraud;
determining a second potential source of fraud based on the identified potential source of fraud; and
in response to the potential source of fraud or the second potential source of fraud being shut down, determining a backup potential source of fraud, the determining the potential source of fraud, the second potential source of fraud, and the backup potential source of fraud using one or more machine learning models, the one or more machine learning models comprising the particular machine learning model;
determining a similarity between the potential source of fraud, the second potential source of fraud, and the backup potential source of fraud with a known instance of fraud;
generating, using natural language processing, an explanation indicating:
the similarity between the potential source of fraud, the second potential source of fraud, and the backup potential source of fraud with the known instance of fraud; and
the particular machine learning model, which has a highest contribution in determining the potential source of fraud, the second potential source of fraud and the backup potential source of fraud;
appending the explanation and the reasoning to a presentation of the potential source of fraud, the second potential source of fraud, and the backup potential source of fraud;
selecting, from among known outcomes of analyses in which veracities of previous potential sources of fraud have been determined, training datasets to train the particular machine learning model, the selecting being based on scenarios associated with the known outcomes that comprise highest uncertainty levels in the particular machine learning model and which increase an accuracy of the particular machine learning model by highest amounts following the training, wherein the training datasets comprise a first training dataset of sources verified to be fraudulent and a second training dataset of sources verified to be non-fraudulent; and
iteratively training the particular machine learning model using the first training dataset and the second training dataset.

12. The system of claim 11, wherein determining the healthcare metric includes converting the amount of opiate doses received by the patient over the period of time into a morphine equivalent.

13. The system of claim 11, wherein the healthcare metric is adjusted based on a size of the patient.

14. The system of claim 11, wherein the healthcare metric includes a patient healthcare metric, the patient healthcare metric characterizing the amount of opiate doses received by the patient over the period of time.

15. The system of claim 11, wherein the healthcare metric includes a healthcare provider healthcare metric, the healthcare provider healthcare metric characterizing the amount of opiate doses received by the patient and one or more other amounts of opiate doses received by one or more other patients over the period of time.

16. A system comprising:
one or more processors; and
a memory storing instructions that, when executed by the one or more processors, in conjunction with a particular machine learning model for a subset of the instructions, cause the system to perform:
analyzing a database of claims;
determining a healthcare metric based on the analyses of the database of claims, the healthcare metric characterizing a billing pattern of one or more healthcare providers;
determining an expected pattern of the healthcare metric in relation to a factor;
comparing, to the expected pattern, an actual pattern of the healthcare metric in relation to the factor;
based on the comparison of the actual pattern of the healthcare metric to the expected pattern, automatically determining a potential source of fraud;
determining a second potential source of fraud based on the identified potential source of fraud;
in response to the potential source of fraud or the second potential source of fraud being shut down, determining a backup potential source of fraud, the determining the potential source of fraud, the second potential source of fraud, and the backup potential source of fraud using one or more machine learning models, the one or more machine learning models comprising the particular machine learning model;
determining a similarity between the potential source of fraud, the second potential source of fraud, and the backup potential source of fraud with a known instance of fraud;
generating, using natural language processing, an explanation indicating:
the similarity between the potential source of fraud, the second potential source of fraud, and the backup potential source of fraud with the known instance of fraud; and the particular machine learning model, which has a highest contribution in determining the potential source of fraud, the second potential source of fraud and the backup potential source of fraud;

appending the explanation and the reasoning to a presentation of the potential source of fraud, the second potential source of fraud, and the backup potential source of fraud;

selecting, from among known outcomes of analyses in which veracities of previous potential sources of fraud have been determined, training datasets to train the particular machine learning model, the selecting being based on scenarios associated with the known outcomes that comprise highest uncertainty levels in the particular machine learning model and which increase an accuracy of the particular machine learning model by highest amounts following the training, wherein the training datasets comprise a first training dataset of sources verified to be fraudulent and a second training dataset of sources verified to be non-fraudulent; and iteratively training the particular machine learning model using the first training dataset and the second training dataset.

17. The system of claim 16, wherein the healthcare metric is determined using a dependence of billings of the one or more healthcare providers on patients seen by the one or more healthcare providers.

18. The system of claim 17, wherein the dependence of billings of the one or more healthcare providers on the patients indicates a level of similarity of tests or treatments among the patients.

19. The system of claim 16, wherein determining the healthcare metric includes determining a level or a periodicity of the one or more healthcare providers' billings that are independent of external factors.

20. The system of claim 16, wherein the expected pattern comprises an expected decrease of the healthcare metric during a period having a weather condition;
   the actual pattern of the healthcare metric comprises an increase during the period having the weather condition; and
   in response to comparing the actual pattern of the healthcare metric to the expected pattern, automatically identifying a potential source of fraud.

* * * * *